(12) United States Patent
Zens

(10) Patent No.: US 6,372,426 B1
(45) Date of Patent: Apr. 16, 2002

(54) IMMUNOASSAY FOR DETERMINING THE AVIDITY OF IMMUNOGLOBULINS

(75) Inventor: Wolfgang Zens, Marburg (DE)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 09/625,059

(22) Filed: Jul. 24, 2000

Related U.S. Application Data

(62) Division of application No. 09/071,292, filed on May 1, 1998, now abandoned.

(30) Foreign Application Priority Data

May 2, 1997 (DE) .......................................... 197 18 361

(51) Int. Cl.[7] .......................... C12Q 1/70; G01N 33/53; G01N 33/566; G01N 33/569
(52) U.S. Cl. .......................... 435/5; 435/7.1; 435/7.22; 435/7.32; 435/962; 436/501
(58) Field of Search ............................ 435/5, 7.1, 7.22, 435/7.32, 962; 436/501, 513, 518

(56) References Cited

U.S. PATENT DOCUMENTS

| | | |
|---|---|---|
| 5,183,901 A | 2/1993 | Login et al. |
| 5,206,385 A | 4/1993 | Login et al. |
| 5,512,659 A | 4/1996 | Ullman et al. ............ 530/391.1 |
| 5,679,537 A | 10/1997 | Newkirk .................... 435/7.92 |
| 5,830,634 A | 11/1998 | Brust et al. .................... 435/5 |

FOREIGN PATENT DOCUMENTS

| | | |
|---|---|---|
| WO | 90/02202 | 3/1990 |
| WO | 97/09619 | 3/1997 |

OTHER PUBLICATIONS

Zusammenfassung, Patent Abstracts of Japan, vol. 012, No. 088 (P–678), Mar. 23, 1988 & JP 62 220865 A (Yatoron :kk), Sep. 29, 1987.

Behring Diagnostics GMBH, Order NO OSEW, Marburg, Germany.

J. Schubert, et al., "Avidity Determination in Epstein–Barr Virus Diagnosis—a Comparison of Immunofluorescence Assay and ELISA", *J. Lab Med.*, vol. 20, No. 12, pp. 713–717, 1996.

J.J. Gray, "Avidityof EBV VCA–specific IgG antibodies: distinction between recent primary infection, past Infection and reactivation", *Journal of Virological Methods*, vol. 52, pp. 95–104, 1995.

J. Polance, et al., "Evaluation of Protein–Denaturing Immunoassays for Avidity of Immunoglobulin G to Rubella Virus", *Journal of Clinical Laboratory Analysis*, vol. 8, pp. 16–21, 1994.

Hillar O. Kangro, et al. "Antibody Avidity Following Varicella–Zoster Virus Infections", *Journal of Medical Virology*, vol. 33, pp. 100–105, 1991.

Primary Examiner—Mary E. Mosher
(74) Attorney, Agent, or Firm—Heller Ehrman White and McAuliffe

(57) ABSTRACT

The present invention relates to a method and a diagnostic aid for the qualitative or quantitative detection of antibodies and for determining their avidity. This makes it possible to diagnose the early phase of viral, bacterial or parasitic infections. The diagnostic aid according to the invention is particularly suitable for automated processing in large analytical laboratories.

10 Claims, 1 Drawing Sheet

Molarity optimization tests with the protein-denaturing substances urea and urea-hydrogen peroxide in the Enzygnost[R] anti-rubella virus IgG ELISA
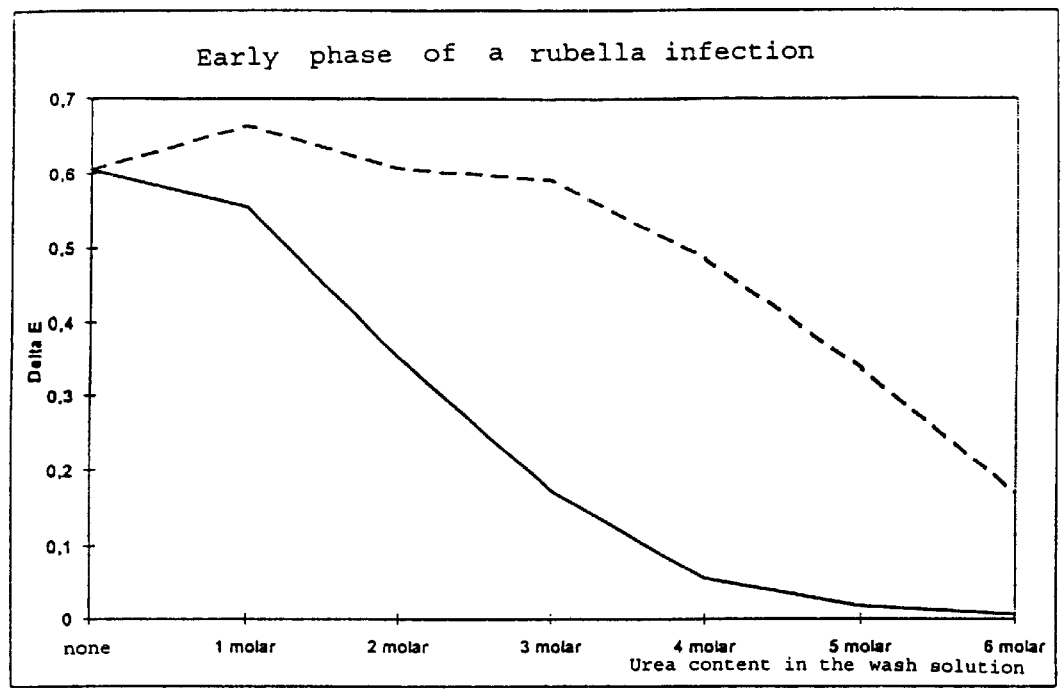
Serum Ab05, serum taken 4 weeks after rubella inoculation
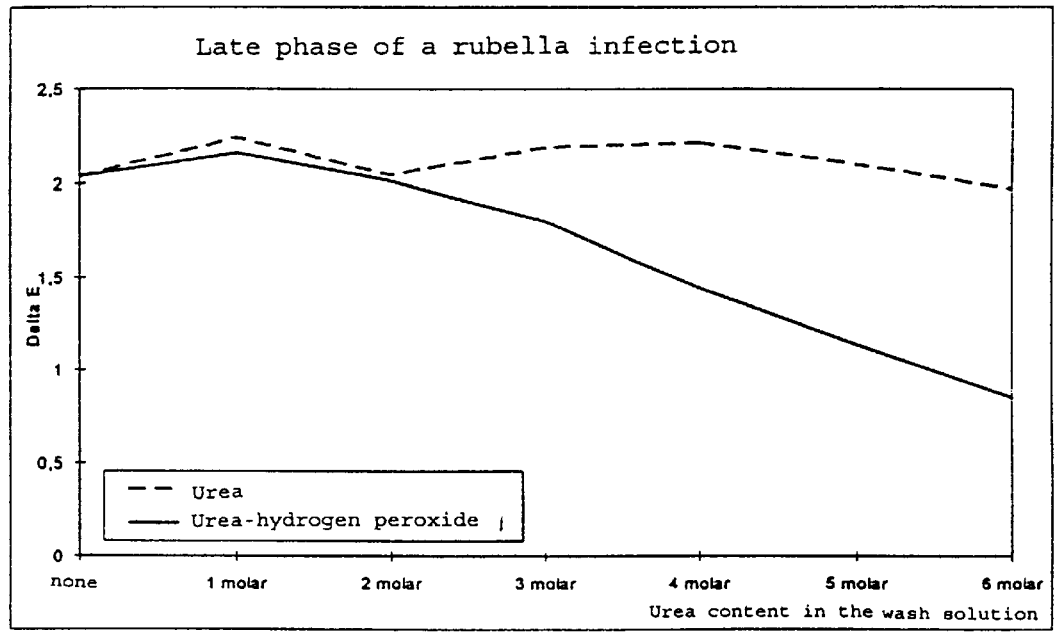
Serum 281, late phase - several years after contact with rubella virus

IMMUNOASSAY FOR DETERMINING THE AVIDITY OF IMMUNOGLOBULINS

This application is a Divisional of application Ser. No. 09/071,292, filed May 1, 1998 abandoned.

The present invention relates to a method and a diagnostic aid for the qualitative or quantitative detection of antibodies and for determining their avidity. This makes it possible to diagnose the early phase of viral, bacterial or parasitic infections. The diagnostic aid according to the invention is particularly suitable for automated processing in large analytical laboratories.

Immunoassays are frequently employed, because of their particularly good specificity and sensitivity, for detecting immunoglobulins in serum and plasma samples for medical diagnostic purposes. In addition, immunoassays are distinguished by being simple to use.

In the case of acute infections, the diagnosis is mainly based on the detection of IgM antibodies. However, cases repeatedly arise in laboratory practice where it is not possible to distinguish reliably between fresh, primary infection and one which has completed its course or has been reactivated without additional investigations. However, it is known that, for example, additional measurement of the avidity of IgG antibodies which are specific for particular viruses, bacteria or parasites makes it possible to assess serological situations which, without this additional measurement, allow no, or only an insufficiently accurate, statement to be made about the time of infection.

Determinations of the avidity of immunoglobulins are carried out in various assay systems, for example in protein-denaturing immunoassays, which are disclosed to the skilled worker inter alia in the following publications: J. Schubert et al. (1996), J. Lab. Med. 20 (12): 713–717; J. J. Gray (1995), J. Virol. Methods 52: 95–104; J. Polanec et al. (1994), J. Clin. Lab. Analysis 8: 16–21; H. O. Kangro et al. (1991), J. Med. Virol. 33: 100–105. Examples of commonly used denaturing substances are urea, diethylamines, guanidines, thiocyanates.

Determination of avidity has already been employed successfully in the diagnosis of viral and nonviral causes of infection, for example Epstein-Barr virus (EBV), rubella virus, cytomegalovirus (CMV), hantavirus, parvovirus B19, varicella zoster virus (VZV), human herpesvirus type 6 (HHV-6), hepatitis C virus (HCV), respiratory syncytial virus (RSV), herpes simplex virus type 1 or 2 (HSV-1/-2) and Toxoplasma gondii. Nevertheless, this method has not become widely used in analytical laboratories because of, amongst other things, technical problems. Three reasons are essentially responsible for this:

1. The substance which is mostly used, urea, is, at the concentration recommended by the authors, on the point of crystallization, which results in frequent blockage of all pipette tips and tubes of equipment for automatic or partly automatic processing of immunoassays (immunoassay processors).
2. If urea solutions of lower molarity (for example 5 to 6 M) are used, the validity of the method is considerably reduced.
3. The range stated in the literature to be marginal or impossible to evaluate for the method is too large.

There has thus been a need to improve known methods for determining the avidity of antibodies. In particular, the applicability to automated immunoassay processes was in need of improvement.

Surprisingly, it has been found within the scope of the present invention that the problems described above can be solved by the possibility of employing the substance, which has not previously been used in protein-denaturing immunoassays, urea-hydrogen peroxide (obtainable, for example, from Carl Roth GmbH+Co Karlsruhe: Article number 7641.1), as protein-denaturing reagent. This substance surprisingly has the property of being as effective in a protein-denaturing immunoassay even at a low molar concentration (approximately 2.5 to 6.5 M) as a high-molar (approximately 6 to 8 M) urea solution. The present invention therefore relates to a method for the qualitative or quantitative detection of an antibody, in which this antibody is brought into contact with the antigen against which it is directed so that immune complexes are able to form, and in which the reaction mixture is brought into contact with a protein-denaturing agent which destabilizes immune complexes containing antibodies of low avidity, while immune complexes containing antibodies of higher avidity are substantially retained, and in which the extent of the binding of the antibody to the antigen is determined by a method known to the skilled worker, wherein the protein-denaturing agent is urea-hydrogen peroxide.

The present invention additionally relates to a method for determining the avidity of an antibody, in which the antibody is brought into contact in a first and a second mixture independently of one another with the antigen against which the antibody is directed so that immune complexes are able to form, and in which one of the two mixtures is brought into contact with a protein-denaturing agent which destabilizes immune complexes containing antibodies of low avidity, while immune complexes containing antibodies of higher avidity are substantially retained, and in which the extent of the binding of the antibody to the antigen in both samples is determined independently of one another by a method known to the skilled worker, and where the avidity of the antibody is revealed by the ratio of the extent of the antigen-antibody bindings in the first and the second mixture, wherein the protein-denaturing agent is urea-hydrogen peroxide.

A preferred method of this type is one in which the antigen is brought into contact, in a form bound to a solid phase, with the antibody, and subsequently washed with a buffer solution containing urea-hydrogen peroxide. Examples of preferred methods of this type include the enzyme immunoassay, radioimmunoassay, Western blot or immunofluorescence assay. However, the skilled worker is aware of other immunoassay systems which can be carried out straightforwardly according to the invention using urea-hydrogen peroxide by means of the present is description.

The abovementioned methods are particularly suitable according to the invention for detecting diagnostically relevant antibodies in body fluids. Antibodies of this type may be directed against viruses, bacteria or parasites such as, for example, EBV, rubella virus, CMV, hantavirus, parvovirus B19, VZV, HHV 6, HBV, HCV, HIV, RSV, HSV-1, HSV-2 or Toxoplasma gondii.

The determination of avidity can advantageously be carried out using commercially obtainable immunoassays (for example ELISA), partly or fully automatically. Another advantage of the present invention is the very good interpretability of the results.

The novel method for determining the avidity of antibodies is particularly suitable for differentiating fresh (i.e. only recently occurring) infections from older (i.e. less recent) infections. In particular, the present invention relates to methods for detecting an acute rubella virus infection, or one which has recently completed its course, a first CMV infection, first EBV infection, first HSV infection or Toxoplasma gondii infection.

The present invention additionally relates to diagnostic aids (diagnostic reagents, assay kits) which are suitable for application of the novel methods described. Diagnostic aids of these types are produced in a manner known per se to the skilled worker, based on the present description of the invention.

BRIEF DESCRIPTION OF THE DRAWING

FIG. 1 shows molarity optimization tests with the protein-denaturing substances urea and urea-hydrogen peroxide in the Enzygnost[R] anti-rubella virus IgG ELISA. Top panel, serum Ab05, serum taken 4 weeks after rubella infection. Bottom panel, serum 281, late phase, several years after contact with rubella virus.

PREPARATION OF THE NOVEL UREA-HYDROGEN PEROXIDE SOLUTION

The wash solution from commercially obtainable ELISA kits is frequently used as diluent solution for protein-denaturing substances. In the following examples, use was made by way of example of the so-called POD wash solution (Order No. OSEW, Behring Diagnostics GmbH, Marburg, Germany). However, any other wash solution suitable in principle for washing an ELISA could have been used. The urea-hydrogen peroxide is used in the range between 2.5 mol/l and 6.5 mol/l, preferably between 4.5 and 6.0 mol/l. The optimized concentration is 5.3 mol/l. It is also conceivable to use urea-hydrogen peroxide in other solutions used for carrying out immunoassays, for example in sample dilution buffers.

Immunoassay Procedure

The abovementioned novel urea-hydrogen peroxide solution is used to carry out an immunoassay, for example an ELISA, by a conventional method.

The modification of the novel method by comparison with known methods is that incubation of the sample is followed by washing twice with a volume suited to the method (for example about 0.3 ml in an ELISA based on microtitre plates) of wash solution containing urea-hydrogen peroxide, and subsequently, for example, washing twice with in each case the same volume of wash solution. The detention time for the wash solution provided by the manufacturer of the automatic equipment does not necessarily require alteration.

The assay is carried out, if automatic operation is required, on an ELISA processor (obtainable, for example, from Behring Diagnostics GmbH).

In the following examples, Behring Diagnostics GmbH ELISAs were used and modified. The POD wash solution was used as wash solution. These examples serve to illustrate the invention further but without restricting it in any way.

EXAMPLES

Example 1

To optimize the ELISA determination of avidity, first the urea washing step and the urea-hydrogen peroxide washing step were compared on sera respectively with fresh or old rubella infection using various reagent molarities.

Result

FIG. 1 shows that the novel urea-hydrogen peroxide solution in a concentration range from 2.5 to 6.5 mol/l achieves the best separation between the two groups of sera.

Example 2

The validity of the novel method with urea-hydrogen peroxide was examined by comparison with the conventional method of the prior art by means of rubella seroconversion.

Result

See Table 1. The ELISA determination of avidity was evaluated according to the novel method as follows: less than or equal to 15% =acute infection, 15 to 20% =tolerance range for acute infection, greater than or equal to 20% =non-recent infection.

TABLE 1

Determination of avid antibodies using wash solution containing urea and containing urea-hydrogen peroxide in the Enzygnost[R] anti-rubella virus IgG assay
Rubella IgM seroconversion (diluted 1:231)

| Sample | Wash solution without urea (mE diff.) | Wash solution with urea (mE diff.) | Avidity index in %[1.)] | Wash solution with urea-$H_2O_2$ (mE diff.) | Avidity index in %[2.)] | IgM signal in mE |
|---|---|---|---|---|---|---|
| Seroconv. Ab 04 3 weeks after inoculation | 163 | 43 | 26.4 | −1 | −0.6 | 681 |
| Seroconv. Ab 05 4 weeks after inoculation | 592 | 305 | 51.5 | 18 | 3.0 | 780 |
| Seroconv. Ab 06 5 weeks after inoculation | 797 | 403 | 50.6 | 27 | 3.4 | 738 |
| Seroconv. Ab 07 8 weeks after inoculation | 1057 | 718 | 67.9 | 97 | 9.2 | 540 |
| Seroconv. Ab 08 14 weeks after inoculation | 1296 | 1008 | 77.8 | 293 | 22.6 | 273 |
| Seroconv. Ab 09 26 weeks after inoculation | 1490 | 1207 | 81.0 | 486 | 32.6 | 202 |

TABLE 1-continued

Determination of avid antibodies using wash solution
containing urea and containing urea-hydrogen peroxide
in the Enzygnost[R] anti-rubella virus IgG assay
Rubella IgM seroconversion (diluted 1:231)

| Sample | Wash solution without urea (mE diff.) | Wash solution with urea (mE diff.) | Avidity index in %[1.)] | Wash solution with urea-$H_2O_2$ (mE diff.) | Avidity index in %[2.)] | IgM signal in mE |
|---|---|---|---|---|---|---|
| Seroconv. Ab 10 54 weeks after inoculation | 1532 | 1340 | 87.5 | 631 | 41.2 | 93 |

[1.)]Assessment of the avidity indices by the method disclosed in the literature
≤15% acute infection
15–40% tolerance for acute infection
40–60% unassessable
≥60% non-recent infection
[2.)]Assessment of the avidity indices
≤15% acute infection
15–20% tolerance for acute infection
≥20% non-recent infection
Calculation of the avidity indices:

$$\text{Avidity index (\%)} = \frac{\text{mE (with urea)} \times 100}{\text{mE (without urea)}}$$

Example 3

The discrimination of the method is to be shown in a group of confirmed rubella IgM-positive sera comparing with a group of confirmed rubella IgM-negative sera.

Result

See Table 2. Most of the sera from the early phase of rubella infection have an avidity index of less than about 5%, whereas most of the rubella sera originating from the late phase of infection have an average avidity index of about 50%.

TABLE 2

Determination of avid antibodies using wash solution
containing urea and containing urea-hydrogen peroxide
in the Enzygnost[R] anti-rubella virus IgG assay

| Sample | Wash solution without urea (mE diff.) | Wash solution with urea (mE diff.) | Avidity index in %[1.)] | Wash solution with urea-$H_2O_2$ (mE diff.) | Avidity index in %[2.)] | IgM signal in mE |
|---|---|---|---|---|---|---|
| Rubella IgM-positive samples (diluted 1:231) | | | | | | |
| DG | 1495 | 1083 | 72.4 | 87 | 5.8 | 631 |
| T 20882 | 433 | 116 | 26.8 | 7 | 1.6 | 1083 |
| 911011-2 | 1014 | 639 | 63.0 | 43 | 4.2 | 472 |
| 240 | 792 | 352 | 44.4 | 22 | 2.8 | 243 |
| 6 DD 416 | 564 | 221 | 39.2 | 6 | 1.1 | 1090 |
| 911011-1 | 666 | 412 | 61.9 | 70 | 10.5 | 642 |
| 242 | 1156 | 887 | 76.7 | 154 | 13.3 | 581 |
| G 23998 | 616 | 270 | 43.8 | 15 | 2.4 | 286 |
| ST 281271 | 1290 | 843 | 65.3 | 20 | 1.6 | 970 |
| 094-1576 | 922 | 469 | 50.9 | 28 | 3.0 | 1210 |
| 6528 | 843 | 407 | 48.3 | 23 | 2.7 | 595 |
| T 40095 | 116 | 57 | 49.1 | 3 | 2.6 | 468 |
| 679 | 1048 | 688 | 65.6 | 39 | 3.7 | 915 |
| DR 6 | 738 | 92 | 12.5 | 2 | 0.3 | 214 |
| Rubella IgM-negative samples (diluted 1:231) | | | | | | |
| 281 | 2067 | 1968 | 95.2 | 1169 | 56.6 | 9 |
| 647957 | 1262 | 1187 | 92.6 | 658 | 51.3 | O.B. |
| 91328 | 497 | 431 | 86.7 | 212 | 42.7 | 28 |
| 144173 | 1039 | 1003 | 96.5 | 475 | 45.7 | 10 |
| 317878 | 246 | 206 | 83.7 | 108 | 43.9 | 22 |
| 144533 | 860 | 758 | 88.1 | 408 | 47.4 | 66 |
| M | 541 | 491 | 90.8 | 180 | 33.3 | 12 |
| 111074 | 2028 | 1804 | 89.0 | 1142 | 56.3 | 56 |

TABLE 2-continued

Determination of avid antibodies using wash solution
containing urea and containing urea-hydrogen peroxide
in the Enzygnost[R] anti-rubella virus IgG assay

| Sample | Wash solution without urea (mE diff.) | Wash solution with urea (mE diff.) | Avidity index in %[1.)] | Wash solution with urea-$H_2O_2$ (mE diff.) | Avidity index in %[2.)] | IgM signal in mE |
|---|---|---|---|---|---|---|
| G 110552 | 1648 | 1632 | 99.0 | 1042 | 63.2 | 32 |
| G 110024 | 1962 | 1924 | 98.1 | 1337 | 68.1 | 16 |

[1.)]Assessment of the avidity indices by the method disclosed in the literature
≦15% acute infection
15–40% tolerance for acute infection
40–60% unassessable
≧60% non-recent infection
[2.)]Assessment of the avidity indices
≦15% acute infection
15–20% tolerance for acute infection
≧20% non-recent infection
Calculation of the avidity indices:

$$\text{Avidity index (\%)} = \frac{\text{mE (with urea)} \times 100}{\text{mE (without urea)}}$$

Example 4

To check Example 3 on the rubella system, the discrimination of the method is to be shown once again taking the example of herpes simplex virus (HSV). A group of confirmed HSV IgM-positive sera is compared with a confirmed HSV IgM-negative group.

Result

See Table 3. Most of the sera from the early phase of herpes simplex infection reach an avidity index of less than about 5%, whereas herpes simplex sera from the late phase of infection have an average avidity index of greater than about 50%.

TABLE 3

Determination of avid antibodies using wash solution
containing urea and containing urea-hydrogen peroxide
in the Enzygnost[R] anti-HSV (herpes simplex virus) IgG assay

| Sample | Wash solution without urea (mE diff.) | Wash solution with urea (mE diff.) | Avidity index in %[1.)] | Wash solution with urea-$H_2O_2$ (mE diff.) | Avidity index in %[2.)] | IgM signal in mE |
|---|---|---|---|---|---|---|
| HSV IgM-positive samples (diluted 1:231) | | | | | | |
| 4398 | 634 | 224 | 35.33 | 3 | 0.47 | 300 |
| 4547 | 1000 | 592 | 59.20 | 78 | 7.20 | 281 |
| 4548 | 939 | 550 | 55.57 | 65 | 6.92 | 203 |
| 42191 | 475 | 20 | 4.21 | −1 | −0.21 | 398 |
| 266317 | 920 | 458 | 49.78 | 40 | 4.35 | 378 |
| 266940 | 831 | 175 | 21.06 | 32 | 3.85 | 390 |
| 266–285 | 428 | 106 | 24.77 | 6 | 1.40 | 426 |
| 306262 | 178 | 38 | 21.35 | 2 | 1.12 | 309 |
| 719.1655 | 364 | 170 | 46.70 | 10 | 2.75 | 249 |
| 634.1864 | 389 | 74 | 19.02 | 5 | 1.29 | 395 |
| 90.1865 | 724 | 203 | 28.04 | 6 | 0.83 | 282 |
| 137.1989 | 449 | 120 | 26.73 | 1 | 0.22 | 302 |
| 993.1989 | 480 | 114 | 23.75 | 2 | 0.42 | 332 |
| 911114 | 376 | 115 | 30.59 | 8 | 2.13 | 233 |
| 43941 | 297 | 38 | 12.79 | 2 | 0.67 | 261 |
| HSV IgM-negative samples (diluted 1:231) | | | | | | |
| 9523 | 1303 | 1285 | 98.62 | 677 | 51.96 | −276 |
| 9954 | 2006 | 2004 | 99.90 | 1126 | 56.13 | 278 |
| 10282 | 1925 | 1771 | 92.00 | 1071 | 55.64 | 221 |
| 10286 | 1909 | 1840 | 96.39 | 1070 | 56.05 | 156 |
| 10307 | 2242 | 2308 | 102.94 | 1534 | 68.42 | 241 |
| 10460 | 2102 | 2089 | 99.38 | 1292 | 61.47 | 535 |
| 10604 | 1942 | 1810 | 93.20 | 1057 | 54.43 | 183 |
| 10660 | 1857 | 1905 | 102.58 | 1089 | 58.64 | 238 |
| 11672 | 1859 | 1795 | 96.56 | 1085 | 58.36 | 190 |
| 11275 | 1834 | 1698 | 92.58 | 782 | 42.64 | 119 |
| 11782 | 2266 | 2245 | 99.07 | 1484 | 65.49 | 481 |

TABLE 3-continued

Determination of avid antibodies using wash solution containing urea and containing urea-hydrogen peroxide in the Enzygnost[R] anti-HSV (herpes simplex virus) IgG assay

| Sample | Wash solution without urea (mE diff.) | Wash solution with urea (mE diff.) | Avidity index in %[1.)] | Wash solution with urea-$H_2O_2$ (mE diff.) | Avidity index in %[2.)] | IgM signal in mE |
|---|---|---|---|---|---|---|
| 11989 | 1784 | 1784 | 100.00 | 904 | 50.67 | 244 |
| 12004 | 1836 | 1870 | 101.85 | 1083 | 58.99 | 221 |
| 12355 | 2302 | 2293 | 99.61 | 1365 | 59.30 | 267 |
| 12496 | 1758 | 1833 | 104.27 | 1028 | 58.48 | 189 |
| 3267 | 1675 | 1757 | 104.90 | 931 | 55.58 | 52 |
| 3590 | 1640 | 1526 | 93.05 | 550 | 33.54 | 207 |

[1.)]Assessment of the avidity indices by the method disclosed in the literature
≦15% acute infection
15–40% tolerance for acute infection
40–60% unassessable
≧60% non-recent infection
[2.)]Assessment of the avidity indices
≦15% acute infection
15–20% tolerance for acute infection
≧20% non-recent infection
Calculation of the avidity indices:

$$\text{Avidity index } (\%) = \frac{mE \text{ (with urea)} \times 100}{mE \text{ (without urea)}}$$

What is claimed is:

1. The method for determining the extent of binding of one or more antibodies to antigen, comprising the steps of:
   (a) bringing said one or more antibodies into contact with said antigen, under conditions which permit immune complexes to form;
   (b) bringing said immune complexes into contact with a urea-hydrogen peroxide protein denaturing agent, wherein the urea-hydrogen peroxide agent is present in a concentration sufficient to substantially destabilize immune complexes containing antibodies of low avidity, but, not sufficient to substantially destabilize immune complexes containing antibodies of high avidity, and
   (c) determining the extent of binding of said one or more antibodies to said antigen.

2. The method of claim 1 wherein said antigen is bound to a solid phase and wherein said urea-hydrogen peroxide protein-denaturing agent is in a buffer solution.

3. The method of claim 1, wherein said measuring is carried out via an enzyme immunoassay, radioimmunoassay, Western blot or immunofluorescence assay.

4. The method of claim 1, wherein said one or more antibodies are obtained from body fluid or fluids.

5. The method of claim 4, wherein said one or more antibodies are directed against viruses, bacteria or parasites.

6. The method of claim 4, wherein said one or more antibodies are directed against EBV, rubella virus, CMV, hantavirus, parvovirus B19, VZV, HHV 6, HBV, HCV, HIV, RSV, HSV-1, HSV-2 or Toxoplasma gondii.

7. The method of claim 1, wherein said urea-hydrogen peroxide is employed in a concentration of from 2.5 to 6.5 M.

8. A method for determining the avidity of one or more antibodies to antigen, comprising the steps of:
   (a) bringing said one or more antibodies into contact with said antigen, under conditions which permit immune complexes to form;
   (b) bringing one mixture of the immune complexes into contact with a urea-hydrogen peroxide protein denaturing agent, wherein the urea-hydrogen peroxide agent is present in a concentration sufficient to substantially destabilize immune complexes containing antibodies of low avidity but not sufficient to substantially destabilize immune complexes containing antibodies of high avidity, and
   (c) comparing the extent of antibody-antigen binding in step (b) to the extent of antibody-antigen binding in a second mixture of said immune complexes not in contact with urea-hydrogen peroxide, wherein the ratio of binding in the presence and absence of urea-hydrogen peroxide indicates the avidity of said one or more antibodies.

9. A method for differentiating a recent infection from an older infection by determining the avidity of an antibody to an antigen according to the method of claim 8, wherein low avidity indicates a recent infection, and high avidity indicates an older infection.

10. The method of claim 9, wherein said infection is a rubella virus infection, a CMV infection, an EBV infection, an HSV infection or a Toxoplasma gondii infection.

* * * * *